United States Patent [19]

Monkiewicz et al.

[11] Patent Number: 5,536,860
[45] Date of Patent: Jul. 16, 1996

[54] PROCESS FOR PREPARING AMINOPROPYLALKOXYSILANES IN THE PRESENCE OF SHAPED POLYMERIC RHODIUM COMPLEX CATALYSTS AND THEIR USE

[75] Inventors: Jaroslaw Monkiewicz; Albert Frings; Michael Horn; Hans-Joachim Koetzsch; Frank Kropfgans; Claus-Dietrich Seiler, all of Rheinfelden; Hans-Guenther Srebny, Duelmen-Rorup; Burkhard Standke, Loerrach, all of Germany

[73] Assignee: Huels Aktiengesellschaft, Marl, Germany

[21] Appl. No.: 538,634

[22] Filed: Oct. 4, 1995

[30] Foreign Application Priority Data

Oct. 4, 1994 [DE] Germany ............. 44 35 390.1

[51] Int. Cl.$^6$ ..................... C07F 7/10
[52] U.S. Cl. .................. 556/413; 556/479
[58] Field of Search ............ 556/413, 479

[56] References Cited

U.S. PATENT DOCUMENTS

| | | |
|---|---|---|
| 4,556,722 | 12/1985 | Quirk et al. . |
| 4,927,949 | 5/1990 | Kabeta et al. . |
| 4,992,573 | 2/1991 | Lewis ........................ 556/479 |
| 5,117,024 | 5/1992 | Dinh et al. ................ 556/413 |
| 5,403,947 | 4/1995 | Shinohara ................. 556/479 |

FOREIGN PATENT DOCUMENTS

| | | |
|---|---|---|
| 0302672 | 2/1989 | European Pat. Off. . |
| 0321174 | 6/1989 | European Pat. Off. . |
| 2189119 | 1/1974 | France . |
| 100267 | 12/1973 | Germany . |

OTHER PUBLICATIONS

Bazant et al., Chemical Abstracts, "Organosilicon Compounds by Hydrosilylation", vol. 80, No. 15, Apr. 15, 1974, p. 426.

Marciniec et al., Chemical Abstracts, "Catalysis of Hyrosilylation Part XIV. Aminoorganosiloxanesilicate–Supported Rhodium Complexes as Catalysts For Hydrosilylation Of Alkenes And Vinylsilanes", vol. 109, No. 11, Sep. 12, 1988, p. 726.

Primary Examiner—Paul F. Shaver
Attorney, Agent, or Firm—Oblon, Spivak, McClelland, Maier & Neustadt

[57] ABSTRACT

Aminopropylalkoxysilanes of formula (I):

$$R^2R^3NCH_2CHR^4CH_2Si(OR)_{3-n}(R^1)_n \qquad (I)$$

are prepared by reacting hydrogensilanes of formula (II):

$$HSi(OR)_{3-n}(R^1)_n \qquad (II)$$

with an amine of formula (III):

$$R^2R^3NCH_2CR^4=CH_2 \qquad (III),$$

where R and $R^1$ are alkyl radicals having from 1 to 8 carbon atoms and n is equal to 0, 1 or 2 and $R^2$ and $R^3$ are hydrogen, alkyl radicals having from 1 to 8 carbon atoms, ω-alkenyl radicals having from 3 to 8 carbon atoms or combinations thereof, and $R^4$ is hydrogen or an alkyl radical having from 1 to 8 carbon atoms, in the presence of a shaped polymeric rhodium complex catalyst containing organosiloxanemonophenylphosphine ligands.

9 Claims, No Drawings

PROCESS FOR PREPARING AMINOPROPYLALKOXYSILANES IN THE PRESENCE OF SHAPED POLYMERIC RHODIUM COMPLEX CATALYSTS AND THEIR USE

BACKGROUND OF THE INVENTION

1. Field of the Invention

The invention relates to a process; for preparing aminopropylalkoxysilanes.

2. Discussion of the Background

Among the group of aminoalkylalkoxysilanes, γ-aminopropyltriethoxysilane in particular finds wide use in industrial applications, for example in the production of glass fibers.

The synthesis of aminopropylalkoxysilanes from allylamine and hydrogensilanes is carried out by known methods in the presence of homogeneously catalyzed systems. Such complex catalysts which are customarily used for carrying out the reaction and are soluble in organic solvents are based on compound of the transition metals cobalt, platinum, rhodium and ruthenium. The reaction product formed contains a regioisomeric mixture of γ-and β-aminopropylalkoxysilanes.

EP-B 0 196 639 teaches a process for preparing aminopropylalkoxysilanes by reaction of a hydrogensilane with allylamine in the presence of a chlorine-free rhodium-triorganophosphorus complex. This homogeneously catalyzed process gives yields of aminopropylalkoxysilanes of from about 60 to 75% and regioisomeric ratios of γ isomer: β isomer of from 6 to 59:1.

Such readily soluble rhodium-organophosphorus complexes, which function as homogeneous catalysts for the preparation of aminopropylalkoxysilanes, do have a high initial activity and selectivity. However, after the reaction is complete and after the distillative separation of the aminosilanes, these catalysts no longer have the activity required for reuse from an economic point of view. The reason for the rapid drop in activity is the dissociation of ligands from the metal complex, often after only a short reaction time. To maintain the activity, considerable excess amounts of the corresponding phosphorus ligands have to be used in the reaction medium.

Other soluble complexes of transition metals of Group VIII of the Periodic Table of the Elements have not achieved any economic importance because of their significantly lower activity and selectivity for the hydrosilylation of allylamines.

A great problem with homogeneously catalyzed processes is the need for maximum recovery of the expensive or environmentally significant transition metals used. The recovery of these metals can often be achieved only by great process effort, otherwise considerable metal losses have to be accepted. Such factors have a considerable influence on the economics and acceptance of a process and the products.

In addition, shaped polymeric complex catalysts of, inter alia, the elements Fe, Co, Ni, Ru, Rh, Pd, Pt, Os and Ir are known. These elements are bridged with one another via phosphorus-containing organosilanes as ligands, with the ligands being coordinately bonded to the respective central atom via strongly bonding phosphorus atoms. The shaped polymeric, in particular spherical, complex rhodium catalysts containing organosiloxanediphenylphosphine or organosiloxanemonophenylphosphine ligands are prepared by a known process. Unlike the $SiO_2$-bonded, heterogeneous catalysts, these complex rhodium catalysts are not synthesized by subsequent application of the transition metal to the support, but by direct condensation of the corresponding transition metal complexes with, for example, tetra-ethoxysilane and aminosilanes, followed by hydrolysis. Such shaped polymeric complex catalysts are described in detail in DE-C 40 35 032 and DE-C 40 35 033, with these shaped polymeric complex catalysts being able to be used to carry out hydroformylation, hydrogenation, oligomerization, carbonylation, hydrosilylation, carboxymethylation, isomerization reactions and for reactions of CO or $CO_2$ with $H_2$. A need, therefore, continues to exist for a process of preparing aminopropylalkoxysilanes which is economically more attractive.

SUMMARY OF THE INVENTION

Accordingly, one object of the invention is to provide a more economical process for preparing aminopropylalkoxysilanes, in which the complex rhodium catalyst can be recovered in a simple manner.

Briefly, this object and other objects of the invention as hereinafter will become more readily apparent can be attained in a process for preparing aminopropylalkoxysilanes of formula (I):

$$R^2R^3NCH_2CHR^4CH_2Si(OR)_{3-n}(R^1)_n \qquad (I)$$

by reacting hydrogensilanes of formula (II):

$$HSi(OR)_{3-n}(R^1)_n \qquad (II)$$

with an amine of formula (III):

$$R^2R^3NCH_2CR^4=CH_2 \qquad (III),$$

wherein R and $R^1$ are alkyl radicals having from 1 to 8 carbon atoms and n is equal to 0, 1 or 2 and $R^2$ and $R^3$ are hydrogen, alkyl radicals having from 1 to 8 carbon atoms, ω-alkenyl radicals having from 3 to 8 carbon atoms and $R^4$ is hydrogen or an alkyl radical having from 1 to 8 carbon atoms, in the presence of a shaped polymeric complex rhodium catalyst containing organosiloxanemonophenylphosphine ligands.

DETAILED DESCRIPTION OF THE PREFERRED EMBODIMENTS

It has now surprisingly been found that aminopropylalkoxysilanes can be prepared very well and particularly economically in the presence of a shaped polymeric complex rhodium catalyst containing organosiloxanemonophenylphosphine ligands, with the catalyst being able to be recovered from the reaction or product mixture in a particularly simple and economical manner. Among the numerous shaped complex transition metal catalysts containing the elements Pd, Pt, Ni, Co, Fe, Ir, Os, Ru and/or Rh as central atoms and having various phosphorus ligands, the shaped polymeric rhodium complex catalyst containing organosiloxanemonophenylphosphine ligands has been found to be particularly advantageous. Thus, in the process of the invention, together with simultaneously high yields, the regioisomeric ratio is established in favor of the preferred γ-aminopropylalkoxysilane isomer.

The present invention further provides for the use of shaped polymeric complex rhodium catalysts containing organosiloxanemonophenylphosphine ligands for the preparation of aminopropylalkoxysilanes.

The process of the invention can be carried out either batchwise or continuously.

The batchwise procedure can be carried out in various ways. Thus, the shaped polymeric complex rhodium catalyst can be initially charged together with hydrogensilane in a reaction vessel (stirred reactor, steel reactor) and the amine component can be added to the suspension; the reverse order can also be employed. It is also possible to initially charge both reactants together, add the catalyst, if desired disperse the catalyst by stirring and subsequently bring the mixture to reaction temperature. The process of the invention requires no particular measures with respect to the use of a protective gas atmosphere, for example to maintain the activity of the catalyst.

When the batchwise procedure is used, the reaction times decrease with increasing catalyst concentration and are from 24 hours to 10 minutes. The rhodium concentration employed in the reaction, based on the amount of hydrogensilane component (II) used, is normally from 50 to 1000 ppm by weight and preferably from 100 to 400 ppm by weight.

In the process of the invention, the shaped polymeric rhodium complex catalyst is normally used in a particle size of from 0.05 to 0.6 mm, preferably in a particle size of from 0.1 to 0.3 mm. The particle size of the shaped polymeric complex rhodium catalyst can be set, for example, by sieving or by means of a classifier or even by mixing individual particle size fractions.

The reaction of hydrogensilanes (II) with an amine (III) in the presence of a shaped polymeric rhodium complex catalyst containing organosiloxanemonophenylphosphine ligands is normally carried out at temperatures of from 90° to 180° C., preferably at temperatures of from 110° to 150° C.

The hydrogensilane (II) is preferably a trialkoxysilane, more preferably a triethoxysilane. The amine (III) is preferably an allylamine.

The shaped polymeric complex rhodium catalyst preferably has a rhodium content of from 0.1 to 3.0% by weight, particular preference being given to using a shaped polymeric complex rhodium catalyst having a rhodium content of from 0.5 to 1.5% by weight.

In some variants of the process of the invention, the use of pressures of up to 40 bar is favorable.

The shaped polymeric complex rhodium catalyst can be easily separated after the reaction is complete, for example by filtration or by decantation. However, it is also possible to first remove the reaction product from the reaction mixture by distillation. The shaped polymeric rhodium complex catalyst can be reused in the process of the invention after a reaction is complete without significant activity loss.

The product obtained according to the process of the invention is composed essentially of a mixture of γ-aminopropylalkoxysilanes and β-aminopropylalkoxysilanes; the γ isomer is here present to an unusually high extent. The γ/β ratio in the crude product allows the γ isomer to be obtained in a purity required for further applications with little distillation effort.

The process of the invention can be carried out continuously in a tube reactor which is to be operated in the flow-through mode, in the circulation mode or in the flow-through mode with substream recirculation. The shaped polymeric complex rhodium catalyst is here located in the catalyst bed of the reactor, e.g., as a loose bed. The catalyst can also be placed in little bags, with such bags being able to be made of a fabric, e.g., a woven wire fabric or braided metal, having an appropriate mesh opening. The bags are then in turn to be introduced individually or linked into the tube reactor and to be fixed.

Such bags arranged individually or linked, filled with shaped polymeric metal complex catalyst, can also be used for the above-described batchwise procedure. This additionally simplifies the recovery of the catalyst from the reaction mixture.

The process of the invention also suppresses the formation of undesired byproducts.

A great advantage of the process of the invention is also that the reaction can be carried out in the absence of solvent. However, should it nevertheless be necessary, the reaction can also be carried out in the presence of an organic solvent or solvent mixture which is inert to the reactants. Possible suitable solvents include, for example, xylene and toluene.

It is most surprising that the process of the invention has not only high chemoselectivity and regioselectivity but also short reaction times and high yields.

Having generally described this invention, a further understanding can be obtained by reference to certain specific examples which are provided herein for purposes of illustration only and are not intended to be limiting unless otherwise specified.

EXAMPLES

Example 1

A 100 ml three-necked flask fitted with magnetic stirrer, condenser, thermometer and dropping funnel is charged with 16.4 g (0.1 mol) of triethoxysilane. 656 mg of DELOXAN HK-I, a commercial product from Degussa, are then added. DELOXAN HK-I is a shaped polymeric complex rhodium catalyst containing organosiloxanemonophenylphosphine ligands. The Rh content of the catalyst material is 1% by weight, which corresponds to an Rh concentration of 400 ppm by weight, based on the amount of triethoxysilane used. The particle size of the catalyst is set to from 0.1 to 0.3 mm, for which purpose the commercial catalyst material DELOXAN HK-I was fractionated by sieving prior to use. The contents of the flask are heated to 135° C. while stirring. When this temperature is reached, 5.7 g (0.1 mol) of allylamine are added dropwise in such a way that the temperature does not fall below 130° C. After the amine addition is complete, the reaction mixture is maintained at 130° C. for a further period of about 30 minutes. After cooling the contents of the flask, the catalyst is separated from the reaction product by filtration. The conversion calculated from the gas chromatogram is about 97% for allylamine and >99% for triethoxysilane. The selectivity of the aminopropyltriethoxysilane formation (γ+β product) is 87.5%. The molar ratio of the γ/β regioisomers is 66:1.

Example 2

A 100 ml three-necked flask fitted with magnetic stirrer, condenser, thermometer and dropping funnel is charged with 16.4 g (0.1 mol) of triethoxysilane. 656 mg of DELOXAM HK-I having an Rh content of 1% by weight, which corresponds to an Rh concentration of 400 ppm by weight, based on the amount of triethoxysilane used, are then added. The particle size of the catalyst material used is 0.1–0.3 mm, as previously described in Example 1. The contents of the flask are heated to 135° C. while stirring. When this temperature is reached, 6.28 g (0.11 mol) of allylamine are added dropwise in such a way that the temperature does not fall below 130° C. After the amine addition is complete, the reaction mixture is maintained at 130° C. for a further period of about 30 minutes. After cooling the contents of the flask, the crude product is distilled off under reduced pressure. The conversion calculated from the gas chromatogram is about 95% for allylamine and >99% for triethoxysilane. The selectivity of the aminopropyltriethoxysilane formation ($\gamma+\beta$ product) is 84.5%. The molar ratio of the $\gamma/\beta$ regioisomers is 65:1.

Examples 3 to 9

The procedure is as described in Example 1, but after each time the catalyst is filtered off from the crude product, the same is reused in the subsequent experiment. The results of the seven experiments carried out successively in this way are shown in Table 1, the reaction times being as shown in the respective experiments.

TABLE 1

Reaction of triethoxysilane (TEOS) with allylamine (molar ratio 1:1) in the presence of DELOXAN HK-I (Rh content 1% by weight, particle size 0.1–0.3 mm) initially charged in suspension, at 135° C.

| Example No. | Reaction Time (min) | Conversion (%) TEOS | Conversion (%) amine | Selectivity (%) $\gamma$ product | Selectivity (%) $\beta$ product |
|---|---|---|---|---|---|
| 3 | 40 | 98 | 98 | 87 | 1.5 |
| 4 | 55 | 95 | 96 | 86 | 1.6 |
| 5 | 70 | 92 | 97 | 83 | 1.5 |
| 6 | 90 | 90 | 93 | 82 | 1.6 |
| 7 | 110 | 86 | 91 | 81 | 1.5 |
| 8 | 190 | 90 | 94 | 80 | 1.4 |
| 9 | 225 | 78 | 88 | 79 | 1.4 |

Examples 10 to 16

The procedure is as described in Example 2, but, after each time the product is distilled from the reaction mixture, the catalyst is reused in the subsequent experiment. The results of the seven experiments carried out successively in this way are shown in Table 2, the reaction times being as shown in the respective experiments.

TABLE 2

Reaction of triethoxysilane (TEOS) with allylamine (molar ratio 1:1.1) in the presence of DELOXAN HK-I (Rh content 1% by weight, particle size 0.1 to 0.3 mm) initially charged in suspension, at 135° C.

| Example No. | Reaction Time (min) | Conversion (%) TEOS | Conversion (%) amine | Selectivity (%) $\gamma$ product | Selectivity (%) $\beta$ product |
|---|---|---|---|---|---|
| 10 | 60 | 99 | 95 | 85 | 1.4 |
| 11 | 75 | 99 | 95 | 87 | 1.6 |
| 12 | 90 | 99 | 95 | 85 | 1.7 |
| 13 | 115 | 97 | 94 | 84 | 1.9 |
| 14 | 135 | 90 | 90 | 79 | 1.9 |
| 15 | 190 | 94 | 94 | 74 | 1.8 |
| 16 | 195 | 83 | 95 | 72 | 1.7 |

Example 17

The procedure is as described in Example 1, but in place of triethoxysilane, allylamine together with the catalyst is initially charged in a closed steel reactor and heated to 140° C. The triethoxysilane is subsequently metered in. The reaction time is 2 hours. The conversion calculated from the gas chromatogram is 96% for allylamine and >99% for triethoxysilane. The selectivity of the aminopropyltriethoxysilane formation ($\gamma+\beta$ product) is 82.5%. The molar ratio of the $\gamma/\beta$ regioisomers is 55:1.

Example 18

The procedure is as described in Example 1, but in place of 400 ppm by weight of rhodium, use is made of only 200 ppm by weight of rhodium, based on the silane component, corresponding to 328 mg of DELOXAN HK-I. The reaction time is 2 hours. The conversion calculated from the gas chromatogram is 99% for allylamine and >99% for triethoxysilane. The selectivity of the aminopropyltriethoxysilane formation ($\gamma+\beta$ product) is 86.3%. The molar ratio of the $\gamma/\beta$ regioisomers is 65:1.

Example 19

The procedure is as described in Example 1, but in place of 400 ppm by weight of rhodium, use is made of only 100 ppm by weight of rhodium, based on the silane component, corresponding to 164 mg of DELOXAN HK-I. The reaction time is extended to 3 hours. The conversion calculated from the gas chromatogram is 96% for allylamine and 94% for triethoxysilane. The selectivity of the aminopropyltriethoxysilane formation ($\gamma+\beta$ product) is 88.5%. The molar ratio of the $\gamma/\beta$ regioisomers is 59:1.

Example 20

The procedure is as indicated in Example 1. 5.18 g (0,055 mol) of diallylamine are used in place of allylamine. The conversion calculated from the gas chromatogram is 98% for both diallylamine and triethoxysilane. The selectivity of the bis(3-triethoxysilylpropyl)amine formation is 47%.

Example 21

A 100 ml three-necked flask, fitted with magnetic stirrer, condenser, thermometer and dropping funnel, is charged with 13.4 g (0.1 mol) of methyldiethoxysilane. 268 mg of DELOXAN HK-I (Rh content 1% by weight, particle size 0.1–0.3 mm; Rh concentration 200 ppm by weight, based on the amount of methyldiethoxysilane) are then added. The contents of the flask are heated to about 100° C. On reaching this temperature, 5.7g (0.1 mol) of allylamine are added dropwise over a period of 1 hour. After the amine addition is complete, the reaction mixture is maintained at 130° C. for 18 hours. After cooling the contents of the flask, the catalyst is separated from the crude product by filtration. The conversion calculated from the gas chromatogram is 96% for allylamine and >94% for methyldiethoxysilane. The selectivity of the aminopropylmethyldiethoxysilane formation ($\gamma+\beta$ product) is 63.4%. The molar ratio of the regioisomers is 45:1.

Example 22

13.4 g (0.1 mol) of methyldiethoxysilane, 5.7 g (0.1 mol) of allylamine and 536 mg of DELOXAN HK-1 (Rh content 1% by weight, particle size 0.1–0.3 mm; Rh concentration of 400 ppm by weight, based on the amount of methyldiethoxysilane used) are placed in a 100 ml steel reactor, provided with magnetic stirrer and manometer. The reactor is heated to about 130° C. while stirring. During this procedure, the internal pressure rises to 6 bar. After a reaction time of 45 minutes, the reactor is cooled to room temperature and the catalyst is separated off by filtration. The conversion calculated from the gas chromatogram is 100% for allylamine and >95% for methyldiethoxysilane. The selectivity of the aminopropylmethyl-diethoxysilane formation ($\gamma+\beta$ product) is 66.3%. The molar ratio of the $\gamma/\beta$ regioisomers is 60:1.

Example 23

A 100 ml steel reactor, fitted with magnetic stirrer and manometer, is charged with 12.2 g (0.1 mol) of trimethoxysilane, 5.7 g (0.1 mol) of allylamine and 732 mg of DELOXAN HK-I (Rh content 1% by weight, particle size 0.1–0.3 mm; Rh concentration 600 ppm by weight, based on the amount of trimethoxysilane). The reactor is heated to 135° C. while stirring. During this procedure, the internal pressure rises to 6 bar. After a reaction time of 6 hours, the reactor is cooled to room temperature and the crude product is separated from the catalyst by filtration. The conversion calculated from the gas chromatogram is 88% for allylamine and >99% for trimethoxyamine. The selectivity of the aminopropyltrimethoxysilane formation ($\gamma+\beta$ product) is 50.2%. The molar ratio of the $\gamma/\beta$ regioisomers is 42:1.

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for preparing aminopropylalkoxysilanes of formula (I):

$$R^2R^3NCH_2CHR^4CH_2Si(OR)_{3-n}(R^1)_n \qquad (I)$$

comprising:

reacting hydrogensilanes of formula (II):

$$HSi(OR)_{3-n}(R^1)_n \qquad (II)$$

with an amine of formula (III):

$$R^2R^3NCH_2CR^4{=}CH_2 \qquad (III),$$

wherein R and $R^1$ are alkyl radicals having from 1 to 8 carbon atoms and n is equal to 0, 1 or 2 and $R^2$ and $R^3$ are hydrogen, alkyl radicals having from 1 to 8 carbon atoms, $\omega$-alkenyl radicals having from 3 to 8 carbon atoms or combination thereof, and $R^4$ is hydrogen or an alkyl radical having from 1 to 8 carbon atoms, in the presence of a shaped polymeric complex rhodium catalyst containing organosiloxanemonophenylphosphine ligands.

2. The process according to claim 1, wherein the shaped polymeric complex rhodium catalyst has a particle size of from 0.05 to 0.6 mm.

3. The process according to claim 1, wherein the shaped polymeric rhodium complex catalyst has a rhodium content of from 0.1 to 3.0% by weight.

4. The process according to claim 1, wherein the rhodium concentration in the reaction is from 50 to 1000 ppm by weight based on the amount of the hydrogensilane component (II).

5. The process according to claim 1, wherein the reaction is carried out at temperatures of from 90° to 180° C.

6. The process according to claim 1, wherein the hydrogensilane (II) is a trialkoxysilane.

7. The process according to claim 1, wherein the amine (III) used is an allylamine.

8. The process according to claim 1, wherein the reaction is carried out in the absence of solvent.

9. The process according to claim 1, wherein the reaction is carried out in the presence of an organic solvent or solvent mixture which is inert to the reactants.

* * * * *